(12) United States Patent
Amon

(10) Patent No.: US 11,051,846 B2
(45) Date of Patent: Jul. 6, 2021

(54) CATHETER DEVICE FOR PROVIDING ACCESS TO A BODY CAVITY OF A PATIENT

(71) Applicant: Fresenius Kabi Deutschland GmbH, Bad Homburg (DE)

(72) Inventor: Barbara Amon, Idstein (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 89 days.

(21) Appl. No.: 16/304,455

(22) PCT Filed: Jun. 21, 2017

(86) PCT No.: PCT/EP2017/065162
§ 371 (c)(1),
(2) Date: Nov. 26, 2018

(87) PCT Pub. No.: WO2017/220624
PCT Pub. Date: Dec. 28, 2017

(65) Prior Publication Data
US 2019/0290320 A1      Sep. 26, 2019

(30) Foreign Application Priority Data
Jun. 24, 2016   (EP) ..................................... 16176155

(51) Int. Cl.
*A61B 17/34*     (2006.01)
*A61J 15/00*     (2006.01)
(Continued)

(52) U.S. Cl.
CPC ....... *A61B 17/3415* (2013.01); *A61J 15/0019* (2013.01); *A61B 2017/00526* (2013.01);
(Continued)

(58) Field of Classification Search
CPC ............ A61J 15/0019; A61M 25/0105; A61M 25/01; A61M 2025/0293; A61B 17/3415;
(Continued)

(56) References Cited

U.S. PATENT DOCUMENTS

2003/0229334 A1   12/2003   Suzuki
2007/0016172 A1    1/2007   Charukhchian

FOREIGN PATENT DOCUMENTS

WO    WO2007/027920 A1    3/2007
WO    WO 2012/061220       5/2012
WO    WO 2014/158399      10/2014

OTHER PUBLICATIONS

FREKA® PEG Set Gastric Instruction Sheets (English version), 6 pages (Jan. 2014).
(Continued)

*Primary Examiner* — Lauren P Farrar
*Assistant Examiner* — Hamza A Darb
(74) *Attorney, Agent, or Firm* — Cook Alex Ltd.

(57) ABSTRACT

A catheter device (1) for providing access to a body cavity of a patient comprises a tube (10) and an inserting shell (11) arranged on the tube (10) and constituted to be fastened to an insertion guide (3) for inserting the catheter device (1) into a body opening (C) of a patient (P). Herein, the inserting shell (11) comprises an opening (111) into which a thread (300) of the insertion guide (3) is insertable for fastening the catheter device (1) to the insertion guide (3). In this way, a catheter device is provided which, in an easy and efficient manner, allows for the fastening to an insertion guide.

9 Claims, 4 Drawing Sheets

(51) Int. Cl.
*A61B 17/00* (2006.01)
*A61M 25/01* (2006.01)

(52) U.S. Cl.
CPC .............. *A61B 2017/00818* (2013.01); *A61M 25/0105* (2013.01)

(58) Field of Classification Search
CPC ........... A61B 2017/00526; A61B 2017/00818; A61B 17/3417
See application file for complete search history.

(56) References Cited

OTHER PUBLICATIONS

International Search Report and Written Opinion, counterpart International Appl. No. PCT/EP2017/065162, dated Sep. 18, 2017 (11 pages).
Search Report, counterpart Chinese App. No. 201780038212.0 (dated Jan. 19, 2021) (2 pages).
First Office Action (with English translation), counterpart Chinese App. No. 201780038212.0 (dated Jan. 28, 2021) (10 pages).

CATHETER DEVICE FOR PROVIDING ACCESS TO A BODY CAVITY OF A PATIENT

The present application is a U.S. National Stage of PCT International Patent Application No. PCT/EP2017/065162, filed Jun. 21, 2017, which claims priority to EP Application No. 16176155, filed Jun. 24, 2016, both of which are hereby incorporated herein by reference.

The invention relates to a catheter device for providing access to a body cavity of a patient according to the preamble of claim 1 and to a method for fastening a catheter device to an insertion guide.

A catheter device of this kind comprises a tube and an inserting shell arranged on the tube. The inserting shell is constituted to be fastened to an insertion guide for inserting the catheter device into a body cavity of a patient.

A catheter device of this kind may for example be used within the context of a so called percutaneous endoscopically-controlled gastrostomy (in short: PEG). Within PEG a catheter device is placed for example in the stomach of a patient to extend through the stomach wall towards the outside to provide an access to the stomach for example for the long-term intragastric feeding of the patient. The catheter device hence provides a puncture cannula to which a feeding line may be connected, such that via the catheter device a feeding solution may be delivered towards the patient for feeding the patient directly into the gastrointestinal tract.

For introducing a catheter device into a cavity of a patient, typically an insertion guide is used. Herein, for example in a first step a puncture cannula is arranged on the stomach wall of the patient via a small incision. Through the puncture cannula the insertion guide is inserted into the stomach of the patient and is grabbed within the stomach by means of an endoscopic device. By means of the endoscopic device the insertion guide is pulled through the puncture cannula on the stomach wall and through the esophagus of the patient to exit through the mouth of the patient. Once the tip of the insertion guide has been pulled out of the mouth of the patient, the catheter device can be fastened to the tip of the insertion guide and can be pulled through the mouth and the esophagus of the patient into the stomach of the patient by pulling on the insertion guide. By means of the insertion guide, thus, the catheter device is guided through the puncture cannula on the stomach wall until it reaches its final position in which it is placed to extend through the stomach wall to provide an access for the feeding of the patient.

Conventionally, for fastening the insertion guide to the catheter device, a thread is provided both on the tip of the insertion guide and on the catheter device. By connecting the threads to each other the insertion guide and the catheter device hence may be coupled to one another, such fastening process however being tedious and time consuming. In addition, the fixation of a thread on the tip of the catheter device may be costly to manufacture.

It is an object of the instant invention to provide a catheter device and a method for fastening a catheter device to an insertion guide which, in an easy and efficient manner, allow for the fastening of the catheter device to the insertion guide.

This object is achieved by means of a catheter device comprising the features of claim 1.

Accordingly, the inserting shell comprises an opening into which a thread of the insertion guide is insertable for fastening the catheter device to the insertion guide.

Hence, the catheter device, on its inserting shell, comprises an opening through which the thread of the insertion guide can be introduced in order to fasten the insertion guide to the catheter device. Hence, there is no need to provide an additional thread on the inserting shell of the catheter device, such that the manufacturing of the catheter device may become easy, with a reduced number of assembly steps and a reduced number of components.

In one embodiment, a channel extends from the opening through the inserting shell towards a notch of the inserting shell. When the thread of the insertion guide is inserted into the channel of the inserting shell, it exits from the channel at the notch and can be fastened to the inserting shell by placing it around the inserting shell. Because no additional components are needed on the inserting shell for fastening the thread to the inserting shell and because the inserting shell can be manufactured as an integral piece for example from a suitable plastics material using an injection molding technique, the manufacturing and assembly of the catheter device may become easy and cost-effective.

The inserting shell, in one aspect, may for example have a conical shape, the opening of the inserting shell being arranged at a tip of the inserting shell.

The thread of the insertion guide may for example form a loophole which, for fastening the insertion guide to the catheter device, is inserted into the opening of the inserting shell to extend through the channel of the inserting shell. Once the loophole exits from the channel at the notch, it can be placed around the inserting shell to extend about an outer circumferential face of the inserting shell. In this way a secure, reliable connection between the insertion guide and the catheter device is established, such that the catheter device can be guided into a patient by pulling on the insertion guide.

To avoid that the thread of the insertion guide, when placed around the inserting shell, protrudes from the outer circumferential face of the inserting shell, in one embodiment a groove is formed on the outer circumferential face of the inserting shell. Within the groove the thread is received, the groove extending about the inserting shell to form a circumferential receptacle for the thread.

The inserting shell is fixed to the tube of the catheter device. For this, the inserting shell may for example, at an end opposite the opening, comprise an insertion piece in the shape of a pin which is engaged with the tube to close off the tube. The insertion piece may for example be bonded to the tube, for example by gluing or welding, such that a fixed connection between the insertion piece of the inserting shell and the tube is established. When pulling on the insertion guide, hence, the tube together with the inserting shell is pulled into the patient such that the catheter device is placed within the cavity of the patient.

In another aspect, an arrangement comprises a catheter device as described above and an insertion guide for inserting the catheter device into a body cavity of a patient. The catheter device and the insertion guide may be delivered from a manufacturer as a set, both the catheter device and the insertion guide forming disposables which, after a one-time use, are to be disposed.

The object is also achieved by means of a method for fastening a catheter device to an insertion guide, the catheter device comprising:
  a tube, and
  an inserting shell arranged on the tube and constituted to be fastened to an insertion guide.

Within the method, a thread of the insertion guide is inserted into an opening of the inserting shell for fastening the catheter device to the insertion guide.

The advantages and advantageous embodiments described above for the catheter device equally apply also to the method such that it shall be referred to the above.

The idea underlying the invention shall subsequently be described in more detail with reference to the embodiment shown in the figures. Herein, FIG. 1 shows a schematic view of a catheter device;

Figure 5A:
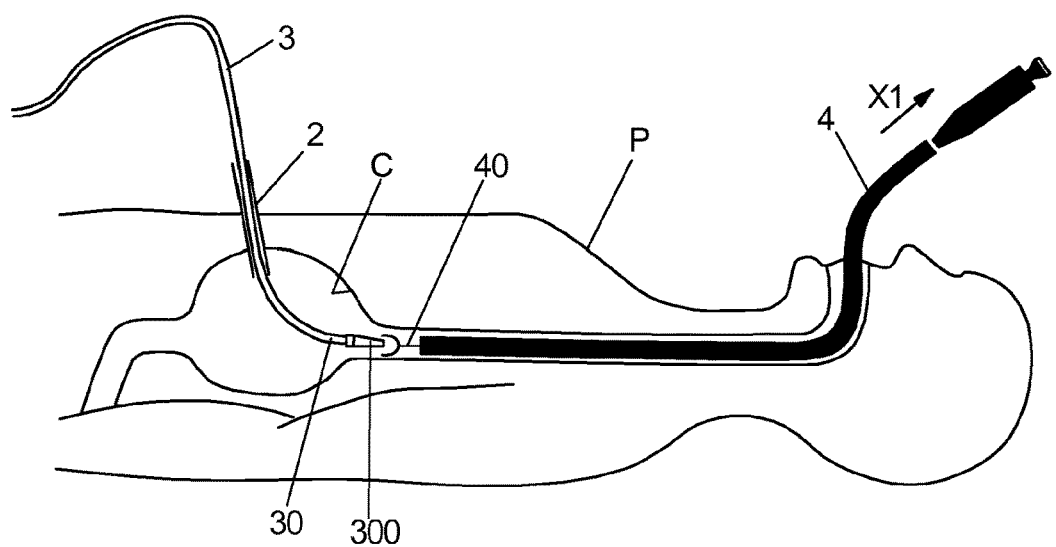
Figure 5B:
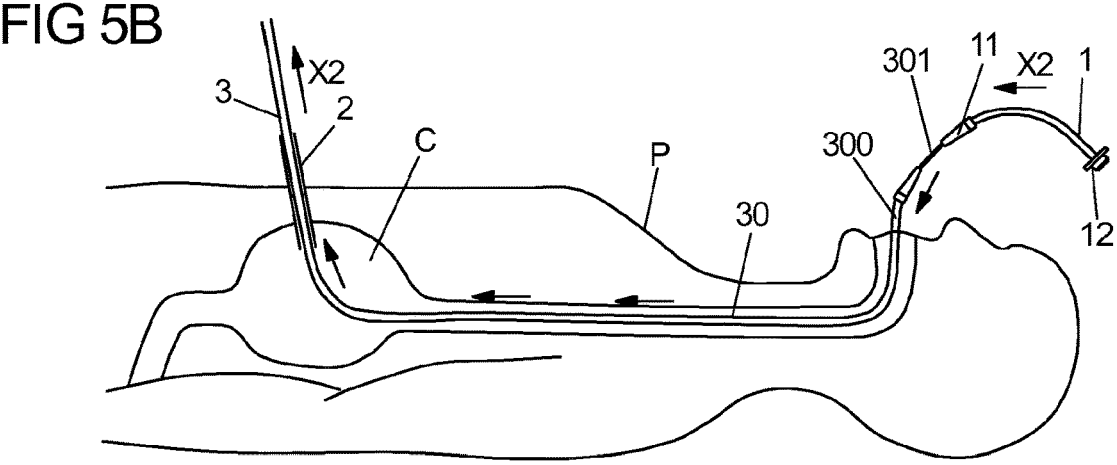
Figure 5C:
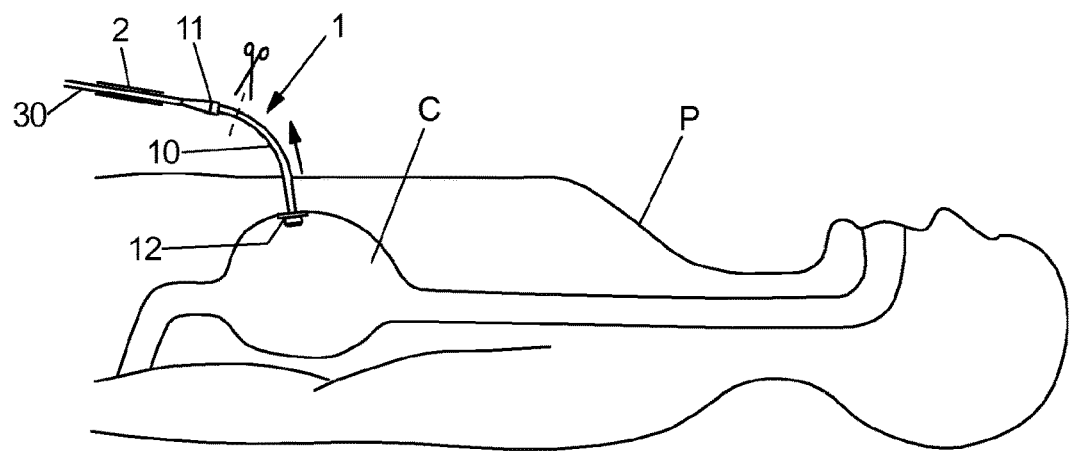
Figure 6C:
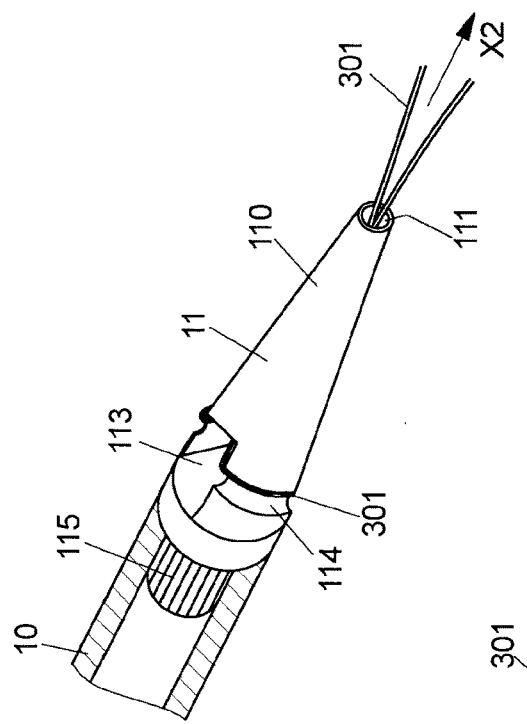
Figure 6B:
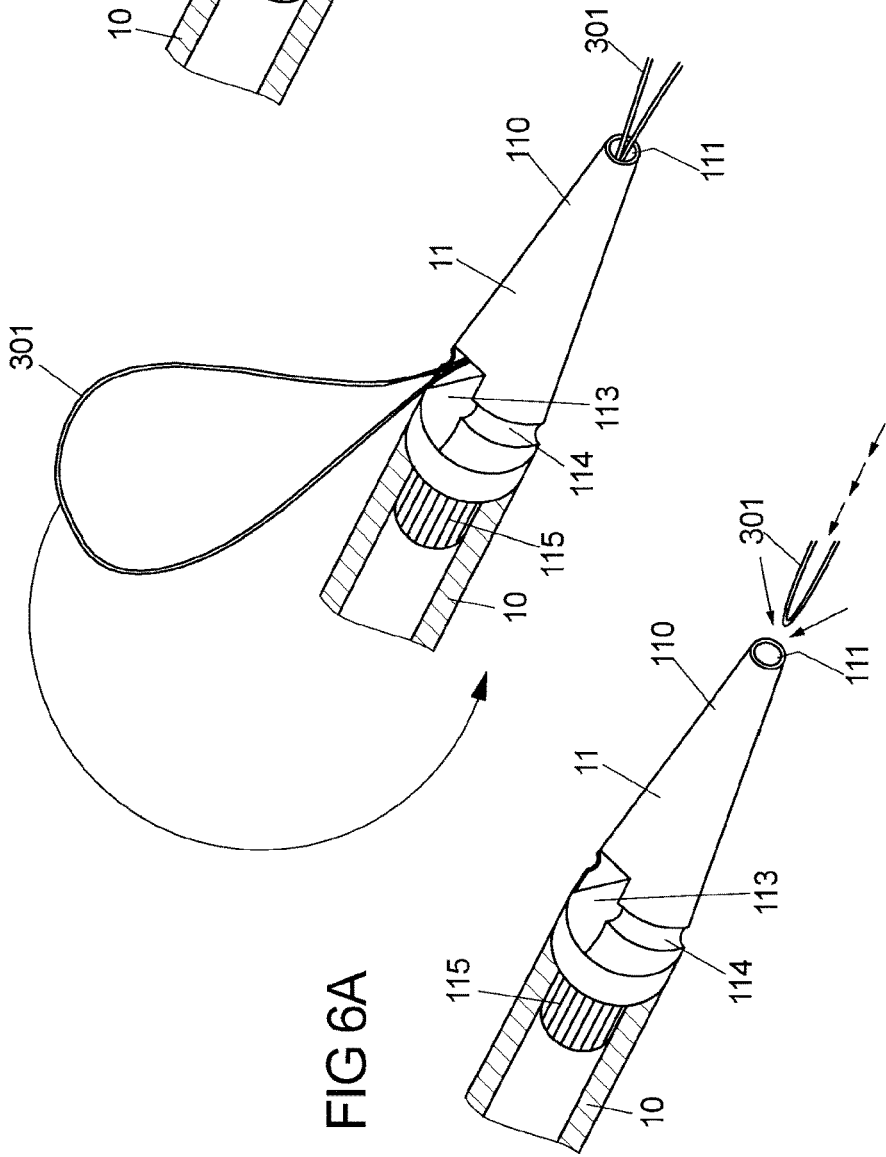
Figure 6A:
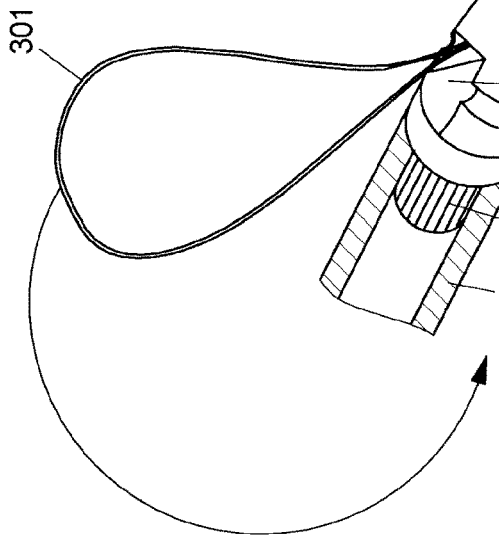

FIGS. 5A-C show views during the insertion of the catheter device into a body cavity of a patient; and FIGS. 6A-C show steps for fastening an insertion guide to the inserting shell of the catheter device.

Figure 1:
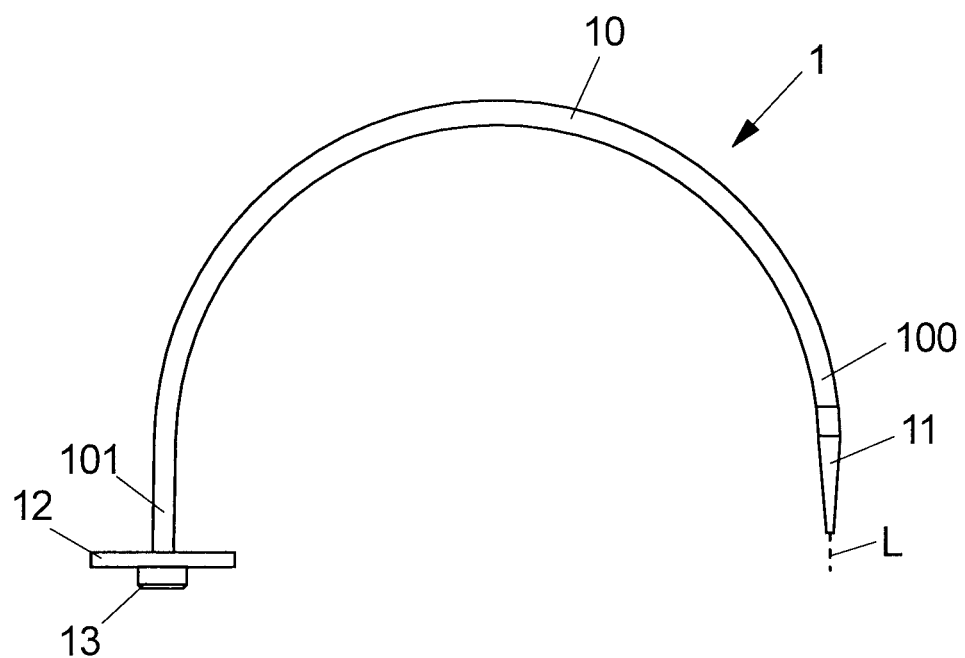

FIG. 1 shows a schematic drawing of a catheter device 1 which is constituted to provide an artificial access to the stomach of a patient for the enteral feeding of the patient.

The catheter device 1 comprises a tube 10 which is made from a flexible biocompatible material such as Polyurethane and at one end 100 carries an inserting shell 11 and at another, second end 101 carries a retention plate 12. As illustrated in FIG. 5C, the catheter device 1 shall be placed within the stomach of a patient P such that the retention plate 12 is arranged inside the stomach C of the patient P in order to retain the catheter device 1 in its position on the patient P, the tube 10 extending through the stomach wall towards the outside such that, via the tube 10, an access for the feeding of the patient P is provided.

The tube 10, as is well-known, comprises an inner lumen providing a channel through which an enteral feeding solution may be delivered towards the patient P. The tube 10, at its end 101, opens into an opening stub 13 which comes to lie inside the stomach C of the patient P such that via the opening stub 13 an enteral feeding solution may flow into the stomach C of the patient P.

The placement of the catheter device 1 on the patient P takes place as illustrated in the sequence of FIGS. 5A to 5C.

To place the catheter device 1 on the patient P to provide an access to the stomach C of the patient P, a puncture cannula 2 is inserted through a small incision in the stomach wall to extend into the stomach C of the patient P. Through the puncture cannula 2, as illustrated in FIG. 5A, an insertion guide 3 is inserted into the stomach C and is grabbed inside the stomach C by a gripper tool 40 of an endoscopic device 4 inserted into the stomach C of the patient P through the mouth and the esophagus of the patient P.

By pulling on the endoscopic device 4 in a pulling direction X1, the endoscopic device 4 is pulled out of the patient P and with it the insertion guide 3 such that the insertion guide 3 is moved through the esophagus to exit through the patient's mouth, as illustrated in FIG. 5B.

The insertion guide 3 serves as a guide device for introducing the catheter device 1 into the patient's stomach C. The insertion guide 3 comprises a line 30 which, when pulling the insertion guide 3 by means of the endoscopic device 4 into the stomach C and through the esophagus of the patient P, is introduced through the puncture cannula 2 to extend through the puncture cannula 2, through the stomach C and through the esophagus of the patient P, as illustrated in FIG. 5B. At a tip 300 of the line 30 a thread 301 is placed which, once the tip 300 is pulled out of the mouth of the patient P as illustrated in FIG. 5B, is fastened to the inserting shell 11 of the catheter device 1, such that the catheter device 1 can be pulled into the mouth of the patient P and through the esophagus of the patient P into the stomach C by pulling on the line 30 of the insertion guide 3 in a reverse pulling direction X2 opposite to the pulling direction X1, as illustrated in FIG. 5B.

By pulling on the line 30 of the insertion guide 3, the catheter device 1 is guided into the mouth of the patient P, through the esophagus of the patient P and finally through the puncture cannula 2 placed on the stomach wall of the patient P, until the catheter device 1 with its retention plate 12 comes into abutment with the inside of the stomach wall, as illustrated in FIG. 5C. Now, the puncture cannula 2 can be removed and the tube 10 can be cut to remove the inserting shell 11 from the tube 10, such that a suitable connector can be placed on the tube 10 for connecting a feeding line to the tube 10 for delivering a feeding solution for the enteral feeding of the patient P.

The fastening of the insertion guide 3 to the catheter device 1 is established via the thread 301 of the insertion guide 3, which for fastening the insertion guide 3 to the catheter device 1 is placed on the inserting shell 11 of the catheter device 1.

Figure 2:
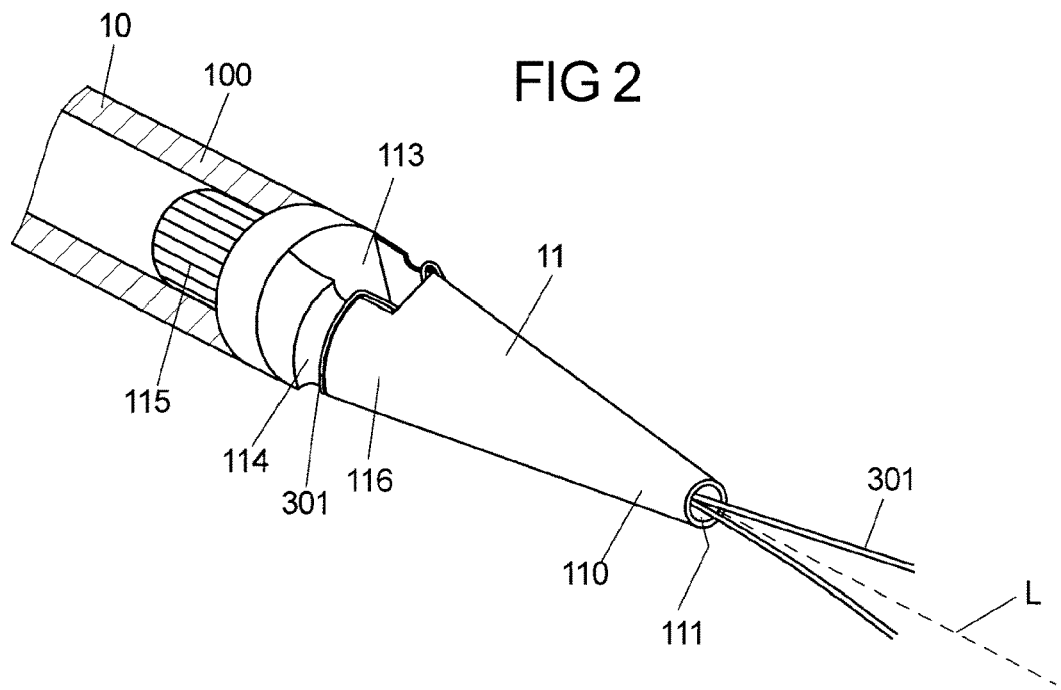
FIG. 2 shows a view of an embodiment of an inserting shell on a tube of the catheter device.
Figure 3:
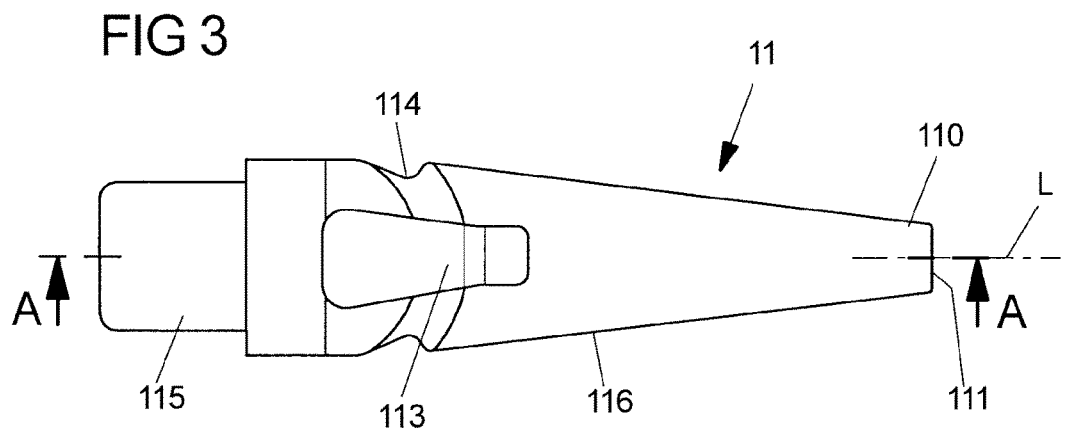
FIG. 3 shows a top view of the inserting shell.
Figure 4:
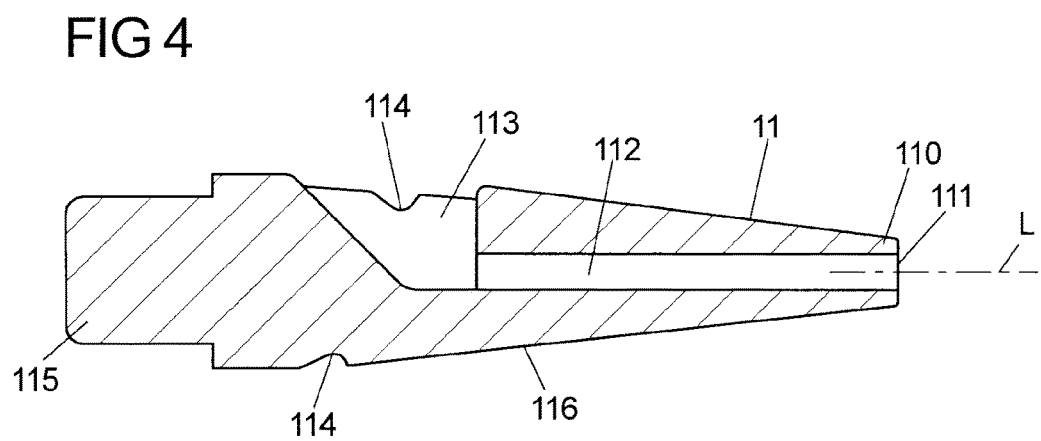
FIG. 4 shows a sectional view of the inserting shell along line A-A according to FIG. 3.

An embodiment of the inserting shell 11 is shown in FIGS. 2 to 4. The inserting shell 11 has a conical shape, with an opening 111 formed at a tip 110 facing away from the tube 10. The inserting shell 11 is made as an integral piece from a plastics material, for example by injection molding, and is inserted into the tube 10 by means of an insertion piece 114 at an end of the inserting shell 11 opposite to the tip 110, such that the tube 10 at its end 100 is closed off by means of the inserting shell 11. Via the insertion piece 115 the inserting shell 11 is bonded to the tube 10 such that a fixed connection between the inserting shell 11 and the tube 10 is established, the bonding being achieved for example by gluing or by welding.

The thread 301 of the insertion guide 3 can be inserted through the opening 111 at the tip 110 of the inserting shell 11 into a channel 112, as it is shown in FIG. 6A. The thread 301 forms a loophole, which is introduced through the channel 112 such that it exits from the channel 112 at a notch 113, as illustrated in FIG. 6B. In this state the loophole of the thread 301 can be placed around the inserting shell 11 as indicated in FIG. 6B, such that it extends about the inserting shell 11 as illustrated in FIG. 2 and FIG. 6C. In this way, a secure, reliable connection between the thread 301 and the inserting shell 11 and, thus, between the insertion guide 3 and the catheter device 1 is established.

In its fastened state, the thread 301 extends about the inserting shell 11. As said, the inserting shell 11 has a conical shape, defined by an outer circumferential face 116 defining a conus extending about a longitudinal axis L. When placed on the inserting shell 11, the thread 301 circumferentially reaches around the outer circumferential face 116 of the inserting shell 11, such that a pulling force in the pulling direction X2 can be transferred to the inserting shell 11 and hence to the catheter device 1.

As visible in FIGS. 2 to 4, a groove 114 extends circumferentially about the inserting shell 11 on the outer circumferential face 116. Within the groove 114 the thread 301 is received such that, when the thread 301 is placed on the inserting shell 11, the thread 301 does not protrude from the outer circumferential wall 116 towards the outside and hence does not present a mechanical resistance when introducing the catheter device 1 through the esophagus into the patient P.

The thread 301 is fixedly connected to the line 30 of the insertion guide 3. Hence, when the thread 301 in the shape of the loophole is placed on the inserting shell 11, the catheter device 1 can be pulled through the patient P by pulling on the line 30, as illustrated in FIG. 5C.

When pulling the inserting shell 11 of the catheter device 1 into the puncture cannula 2, the inserting shell 11 may, in one embodiment, enter into the puncture cannula 2 and may come into operative connection with the puncture cannula 2, as this is illustrated in FIG. 5C. The inserting shell 11 hence becomes stuck in the puncture cannula 2 such that it pulls the puncture cannula 2 with it and out of its position on the stomach wall. The puncture cannula 2 hence is automatically removed from the stomach wall when pulling the catheter device 1 into its position on the stomach wall.

With the proposed catheter device 1, an easy to establish, yet reliable connection of the insertion guide 3 to the catheter device 1 can be established. The connection herein is established using a minimum number of components. In particular, no further components on the catheter device 1 beyond the inserting shell 11 are needed. In particular, an additional thread on the inserting shell 11, as conventionally used, is not required.

The idea underlying the invention is not limited to the embodiments described above, but can be implemented in entirely different embodiments in a similar fashion.

A catheter device of the described kind is not limited to a gastrostomy, but may in principle be used also for example for a gastrojejunostomy for providing an access to the jejunum of the patient. Other uses of the catheter device of the described kind are conceivable.

LIST OF REFERENCE NUMERALS

1 Catheter device
10 Tube
100, 101 End
11 Inserting shell
110 Tip
111 Opening
112 Channel
113 Notch
114 Groove
115 Insertion piece
116 Outer circumferential face
12 Retention plate
13 Opening stub
2 Puncture cannula
3 Insertion guide
30 Line
300 Tip
301 Thread
4 Endoscopic device
40 Gripper tool
C Body cavity
L Longitudinal axis
P Patient
X1, X2 Pulling direction

The invention claimed is:

1. A catheter device for providing access to a body cavity of a patient, comprising:
   a tube, and
   an inserting shell arranged on the tube and configured to be fastened to an insertion guide for inserting the catheter device into the body cavity of the patient,
   wherein the inserting shell comprises an opening into which a thread of the insertion guide is insertable for fastening the catheter device to the insertion guide, and
   wherein the inserting shell comprises a groove formed on an outer circumferential face of the inserting shell and extending around a circumference of the inserting shell, the groove configured to form a circumferential receptacle for the thread and to receive the thread therein, the thread forming a loophole placeable around the circumference of the inserting shell to extend around the outer circumferential face of the inserting shell.

2. The catheter device according to claim 1, wherein from the opening a channel extends through the inserting shell towards a notch of the inserting shell, the thread being insertable through the channel to exit the channel at the notch.

3. The catheter device according to claim 1, wherein the inserting shell has a conical shape, the opening being arranged at a tip of the inserting shell.

4. The catheter device according to claim 1, wherein the inserting shell, at an end opposite the opening, comprises an insertion piece engaged with the tube and closing the tube at an end of the tube.

5. The catheter device according to claim 4, wherein the insertion piece is bonded to the tube.

6. The catheter device according to claim 5, wherein the insertion piece is glued or welded to the tube.

7. An arrangement, comprising a catheter device according to claim 1 and the insertion guide for inserting the catheter device into the body cavity of the patient, wherein the thread of the insertion guide forms a loophole placeable around the circumference of the inserting shell to extend around the outer circumferential face of the inserting shell.

8. The catheter device according to claim 1, wherein the groove is configured to receive the thread without the thread protruding from the groove.

9. A method for fastening a catheter device to an insertion guide, the catheter device comprising a tube, and an inserting shell arranged on the tube and configured to be fastened to an insertion guide, the method comprising:
   inserting a thread of the insertion guide into an opening of the inserting shell for fastening the catheter device to the insertion guide, and
   placing a loophole formed from the thread around a circumference of the inserting shell to extend around an outer circumferential face of the inserting shell, the inserting shell comprising a groove formed on the outer circumferential face of the inserting shell and extending around the circumference of the inserting shell, the groove configured to form a circumferential receptacle for the thread and to receive the thread therein.

* * * * *